US009854962B2

(12) United States Patent  
McGrail et al.

(10) Patent No.: US 9,854,962 B2  
(45) Date of Patent: Jan. 2, 2018

(54) VISUALIZATION INSTRUMENT

(75) Inventors: Thomas W. McGrail, Cicero, IN (US); Michael S. Pargett, West Lafayette, IN (US); David J. Miller, Noblesville, IN (US); Yun Siung Tony Yeh, Libertyville, IL (US); Randal B. Chinnock, Eastford, CT (US); George Grubner, Needham, MA (US); Elizabeth Powell Goodrich, Roslidale, MA (US); Paul Crosby Gregory, Watertown, MA (US); Gary Vincent Palladino, Cambridge, MA (US); Brian Hack, Cambridge, MA (US); Kristin Jugenheimer Size, Waltham, MA (US); Richard L. Miller, Needham, MA (US)

(73) Assignee: King Systems Corporation, Noblesville, IN (US)

( * ) Notice: Subject to any disclaimer, the term of this patent is extended or adjusted under 35 U.S.C. 154(b) by 645 days.

(21) Appl. No.: 12/874,058

(22) Filed: Sep. 1, 2010

(65) Prior Publication Data

US 2011/0130627 A1  Jun. 2, 2011

Related U.S. Application Data

(60) Provisional application No. 61/314,058, filed on Mar. 15, 2010, provisional application No. 61/265,330, filed on Nov. 30, 2009.

(51) Int. Cl.
*A61B 1/00* (2006.01)
*A61B 1/267* (2006.01)
(Continued)

(52) U.S. Cl.
CPC .......... *A61B 1/267* (2013.01); *A61B 1/00016* (2013.01); *A61B 1/00052* (2013.01); (Continued)

(58) Field of Classification Search
CPC ... A61B 1/267; A61B 1/2673; A61B 1/00016; A61B 1/00052; A61B 1/00103; (Continued)

(56) References Cited

U.S. PATENT DOCUMENTS 3,625,793 A * 12/1971 Sheridan ............. A61M 25/001  
156/229  
3,766,909 A    10/1973 Ozbey  
(Continued)

FOREIGN PATENT DOCUMENTS

EP    1640033    3/2006  
EP    1977685    10/2008  
(Continued)

OTHER PUBLICATIONS

International Search Report and Written Opinion for PCT Application No. PCT/US2010/058226, Jun. 1, 2011, 16 pgs.  
(Continued)

*Primary Examiner* — John P Leubecker  
*Assistant Examiner* — Rajaa El Alami  
(74) *Attorney, Agent, or Firm* — Faegre Baker Daniels LLP (57) ABSTRACT

A visualization instrument comprising a display support component removably coupled to a component insertable into a target space. The insertable component includes a camera providing images of the target space. The images are presented in a display device supported by the display support component. The insertable component may be discarded after a permitted number of uses.

39 Claims, 7 Drawing Sheets

(51) Int. Cl.
*A61B 1/05* (2006.01)
*G02B 23/24* (2006.01)
*A61B 1/018* (2006.01)

(52) U.S. Cl.
CPC ...... *A61B 1/00103* (2013.01); *A61B 1/00105* (2013.01); *A61B 1/05* (2013.01); *G02B 23/2423* (2013.01); *G02B 23/2446* (2013.01); *A61B 1/018* (2013.01)

(58) Field of Classification Search
CPC ..... A61B 1/00105; A61B 1/05; A61B 1/3423; A61B 1/3431; G02B 23/2423; G02B 23/2446; G02B 1/018
USPC ....... 600/109, 187, 188, 190, 194, 114, 122, 600/131, 139, 146, 160, 169, 171, 175, 600/185
See application file for complete search history.

(56) References Cited

U.S. PATENT DOCUMENTS

| | | |
|---|---|---|
| 3,771,514 A | 11/1973 | Huffman et al. |
| 4,090,518 A * | 5/1978 | Elam ................... A61M 16/04 128/207.15 |
| 4,114,609 A | 9/1978 | Moses |
| 4,126,127 A | 11/1978 | May |
| 4,167,946 A * | 9/1979 | Sandstrom ............ A61M 25/02 128/207.17 |
| 4,231,365 A * | 11/1980 | Scarberry ............ A61M 16/04 128/207.15 |
| 4,360,008 A | 11/1982 | Corazzelli, Jr. |
| 4,573,451 A | 3/1986 | Bauman |
| 4,592,343 A | 6/1986 | Upsher |
| 4,611,579 A | 9/1986 | Bellhouse |
| 4,616,631 A * | 10/1986 | Takahashi .......... A61B 1/00073 600/139 |
| 4,742,819 A | 5/1988 | George |
| 4,793,327 A | 12/1988 | Frankel |
| 4,832,004 A | 5/1989 | Heckele |
| 4,846,153 A | 7/1989 | Berci |
| 4,947,896 A | 8/1990 | Bartlett |
| 4,982,729 A | 1/1991 | Wu |
| 5,003,962 A | 4/1991 | Choi |
| 5,016,614 A | 5/1991 | MacAllister |
| 5,038,766 A | 8/1991 | Parker |
| 5,042,469 A | 8/1991 | Augustine |
| 5,095,888 A | 3/1992 | Hawley |
| 5,183,031 A | 2/1993 | Rossoff |
| 5,202,795 A | 4/1993 | Kashima |
| 5,203,320 A | 4/1993 | Augustine |
| 5,261,392 A | 11/1993 | Wu |
| 5,287,848 A | 2/1994 | Cubb et al. |
| 5,329,940 A | 7/1994 | Adair |
| 5,339,805 A | 8/1994 | Parker |
| 5,363,838 A | 11/1994 | George |
| 5,381,787 A | 1/1995 | Bullard |
| 5,400,771 A | 3/1995 | Pirak et al. |
| 5,431,152 A | 7/1995 | Flam et al. |
| 5,443,058 A | 8/1995 | Ough |
| 5,489,256 A | 2/1996 | Adair |
| 5,498,231 A | 3/1996 | Franicevic |
| 5,513,627 A | 5/1996 | Flam |
| 5,551,946 A | 9/1996 | Bullard |
| 5,603,688 A | 2/1997 | Upsher |
| 5,607,386 A * | 3/1997 | Flam ................... A61B 1/2676 128/200.26 |
| 5,607,435 A * | 3/1997 | Sachdeva ............ A61B 1/0058 359/819 |
| 5,643,175 A | 7/1997 | Adair |
| 5,645,519 A * | 7/1997 | Lee ..................... A61B 1/303 600/114 |
| 5,665,052 A | 9/1997 | Bullard |
| 5,676,635 A | 10/1997 | Levin |
| 5,716,323 A | 2/1998 | Lee |
| 5,776,052 A | 7/1998 | Callahan |
| 5,800,344 A | 9/1998 | Wood, Sr. et al. |
| 5,803,898 A | 9/1998 | Bashour |
| 5,819,733 A | 10/1998 | Bertram |
| 5,827,178 A | 10/1998 | Berall |
| 5,842,973 A | 12/1998 | Bullard |
| 5,845,634 A | 12/1998 | Parker |
| 5,873,814 A | 2/1999 | Adair |
| 5,879,289 A | 3/1999 | Yarush et al. |
| 5,913,817 A | 6/1999 | Lee |
| 5,929,901 A | 7/1999 | Adair et al. |
| 5,986,693 A | 11/1999 | Adair et al. |
| 6,043,839 A | 3/2000 | Adair et al. |
| 6,046,769 A | 4/2000 | Ikeda et al. |
| 6,079,409 A | 6/2000 | Brain |
| 6,097,423 A | 8/2000 | Boze et al. |
| 6,099,465 A | 8/2000 | Inoue |
| 6,115,523 A | 9/2000 | Choi et al. |
| 6,142,144 A | 11/2000 | Pacey |
| 6,174,281 B1 | 1/2001 | Abramowitz |
| 6,190,308 B1 | 2/2001 | Irion et al. |
| 6,248,061 B1 | 6/2001 | Cook, Jr. |
| 6,275,255 B1 | 8/2001 | Adair et al. |
| 6,310,642 B1 | 10/2001 | Adair et al. |
| 6,322,498 B1 | 11/2001 | Gravenstein et al. |
| 6,354,993 B1 | 3/2002 | Kaplan et al. |
| 6,396,873 B1 | 5/2002 | Goldstein et al. |
| 6,413,209 B1 | 7/2002 | Thompson |
| 6,432,042 B1 | 8/2002 | Bashour |
| 6,432,046 B1 | 8/2002 | Yarush et al. |
| 6,439,232 B1 * | 8/2002 | Brain ................... A61M 16/04 128/200.26 |
| 6,449,007 B1 | 9/2002 | Yokoyama |
| 6,494,826 B1 | 12/2002 | Chatenever et al. |
| 6,494,828 B1 | 12/2002 | Berall |
| 6,543,447 B2 * | 4/2003 | Pacey ..................... A61B 1/05 128/200.26 |
| 6,623,425 B2 | 9/2003 | Cartledge et al. |
| 6,652,453 B2 | 11/2003 | Smith et al. |
| 6,655,377 B2 * | 12/2003 | Pacey ................. A61B 1/2676 128/200.26 |
| 6,656,110 B1 | 12/2003 | Irion et al. |
| 6,663,560 B2 | 12/2003 | MacAulay et al. |
| 6,676,598 B2 | 1/2004 | Rudischhauser |
| 6,750,037 B2 | 6/2004 | Adair et al. |
| 6,753,160 B2 | 6/2004 | Adair et al. |
| 6,792,948 B2 | 9/2004 | Brain |
| 6,830,049 B2 | 12/2004 | Augustine et al. |
| 6,832,986 B2 | 12/2004 | Chhibber et al. |
| 6,840,903 B2 | 1/2005 | Mazzei et al. |
| 6,843,769 B1 | 1/2005 | Gandarias |
| 6,860,264 B2 * | 3/2005 | Christopher .......... A61M 16/04 128/200.26 |
| 6,870,566 B1 | 3/2005 | Koide et al. |
| 6,875,169 B2 | 4/2005 | Berci et al. |
| 6,890,298 B2 | 5/2005 | Berci et al. |
| 6,901,928 B2 | 6/2005 | Loubser |
| 6,923,663 B2 | 8/2005 | Oddsen et al. |
| 6,929,600 B2 | 8/2005 | Hill |
| 6,982,740 B2 | 1/2006 | Adair |
| 6,982,742 B2 | 1/2006 | Adair |
| 6,984,205 B2 | 1/2006 | Gazdzinski |
| 7,030,904 B2 | 4/2006 | Adair et al. |
| 7,044,910 B2 | 5/2006 | Cartledge et al. |
| 7,048,686 B2 | 5/2006 | Kameya et al. |
| 7,110,808 B2 | 9/2006 | Adair |
| 7,116,352 B2 | 10/2006 | Yaron |
| 7,128,071 B2 | 10/2006 | Brain |
| 7,134,992 B2 | 11/2006 | Schara et al. |
| 7,154,527 B1 | 12/2006 | Goldstein et al. |
| D534,652 S | 1/2007 | McGrath |
| 7,156,091 B2 | 1/2007 | Koyama et al. |
| 7,159,589 B2 | 1/2007 | Brain |
| 7,182,728 B2 | 2/2007 | Cubb et al. |
| RE39,508 E * | 3/2007 | Parker ............... A61M 16/0488 128/200.26 |
| 7,212,227 B2 | 5/2007 | Amling et al. |
| 7,243,653 B2 | 7/2007 | Nelson |

(56) References Cited

U.S. PATENT DOCUMENTS

| | | | |
|---|---|---|---|
| 7,278,420 B2* | 10/2007 | Ganesh | A61M 16/04 128/200.26 |
| 7,289,139 B2 | 10/2007 | Amling et al. | |
| 7,297,105 B2 | 11/2007 | Mackin | |
| 7,305,985 B2 | 12/2007 | Brain | |
| 7,369,176 B2 | 5/2008 | Sonnenschein | |
| 7,383,599 B2 | 6/2008 | Gabbay | |
| 7,448,377 B2 | 11/2008 | Koyama et al. | |
| 7,471,310 B2 | 12/2008 | Amling et al. | |
| 7,480,402 B2 | 1/2009 | Bar/Zohar et al. | |
| 7,485,375 B2 | 2/2009 | Tokuda et al. | |
| 7,493,901 B2 | 2/2009 | Brain | |
| 7,511,732 B2 | 3/2009 | Ellison et al. | |
| 7,563,227 B2 | 7/2009 | Gardner | |
| 7,658,708 B2 | 2/2010 | Schwartz et al. | |
| 7,683,926 B2 | 3/2010 | Schechterman et al. | |
| 7,771,350 B2 | 8/2010 | Geist et al. | |
| 7,909,757 B2 | 3/2011 | Herman | |
| 7,909,759 B2 | 3/2011 | Pecherer | |
| 7,946,981 B1 | 5/2011 | Cubb | |
| 8,029,440 B2* | 10/2011 | Birnkrant et al. | 600/188 |
| 8,894,570 B2* | 11/2014 | Jiang | A61B 1/00052 600/194 |
| 8,998,798 B2* | 4/2015 | Hayman | A61B 1/00045 600/120 |
| 9,415,179 B2* | 8/2016 | Molnar | A61B 7/003 |
| 9,421,341 B2* | 8/2016 | Miller | A61M 16/0463 |
| 2001/0004768 A1 | 6/2001 | Hodge et al. | |
| 2001/0012923 A1* | 8/2001 | Christopher | A61M 16/0488 604/48 |
| 2001/0013345 A1 | 8/2001 | Bertram | |
| 2001/0014768 A1 | 8/2001 | Kaplan et al. | |
| 2001/0033326 A1 | 10/2001 | Goldstein et al. | |
| 2001/0054425 A1* | 12/2001 | Bertram | A61M 16/04 128/207.15 |
| 2002/0010417 A1 | 1/2002 | Bertram | |
| 2002/0022769 A1 | 2/2002 | Smith | |
| 2002/0103494 A1 | 8/2002 | Pacey | |
| 2003/0183234 A1* | 10/2003 | Ranzinger | A61M 16/04 128/207.15 |
| 2003/0195390 A1 | 10/2003 | Graumann | |
| 2004/0019256 A1 | 1/2004 | Cubb | |
| 2004/0028390 A9 | 2/2004 | Chatenever et al. | |
| 2004/0122292 A1 | 6/2004 | Dey et al. | |
| 2004/0127770 A1 | 7/2004 | McGrath | |
| 2004/0133072 A1 | 7/2004 | Kennedy | |
| 2004/0215061 A1 | 10/2004 | Kimmel et al. | |
| 2005/0059863 A1 | 3/2005 | Zilch | |
| 2005/0080342 A1 | 4/2005 | Gilreath et al. | |
| 2005/0090712 A1* | 4/2005 | Cubb | A61B 1/00073 600/120 |
| 2005/0090715 A1 | 4/2005 | Schorer | |
| 2005/0139220 A1* | 6/2005 | Christopher | A61M 16/04 128/207.14 |
| 2005/0159649 A1 | 7/2005 | Patel | |
| 2005/0182297 A1 | 8/2005 | Gravenstein et al. | |
| 2005/0187434 A1 | 8/2005 | Dey et al. | |
| 2005/0192481 A1 | 9/2005 | Berci et al. | |
| 2005/0240081 A1 | 10/2005 | Eliachar | |
| 2005/0244801 A1 | 11/2005 | DeSalvo | |
| 2005/0279355 A1 | 12/2005 | Loubser | |
| 2006/0004258 A1 | 1/2006 | Sun et al. | |
| 2006/0004260 A1 | 1/2006 | Boedeker et al. | |
| 2006/0015008 A1 | 1/2006 | Kennedy | |
| 2006/0020166 A1 | 1/2006 | Berall | |
| 2006/0020171 A1 | 1/2006 | Gilreath | |
| 2006/0022234 A1 | 2/2006 | Adair et al. | |
| 2006/0050144 A1 | 3/2006 | Kennedy | |
| 2006/0079734 A1 | 4/2006 | Miyagi | |
| 2006/0119621 A1 | 6/2006 | Krier | |
| 2006/0162730 A1 | 7/2006 | Glassenberg et al. | |
| 2006/0180155 A1 | 8/2006 | Glassenberg et al. | |
| 2006/0241476 A1 | 10/2006 | Loubser | |
| 2006/0276693 A1 | 12/2006 | Pacey | |
| 2006/0276694 A1 | 12/2006 | Gandarias | |
| 2007/0024717 A1 | 2/2007 | Chatenever et al. | |
| 2007/0030345 A1 | 2/2007 | Amling et al. | |
| 2007/0049794 A1 | 3/2007 | Glassenberg et al. | |
| 2007/0068530 A1 | 3/2007 | Pacey | |
| 2007/0074728 A1 | 4/2007 | Rea | |
| 2007/0093693 A1 | 4/2007 | Geist et al. | |
| 2007/0095352 A1 | 5/2007 | Berall | |
| 2007/0106117 A1 | 5/2007 | Yokota | |
| 2007/0106121 A1* | 5/2007 | Yokota et al. | 600/188 |
| 2007/0106122 A1 | 5/2007 | Yokota et al. | |
| 2007/0118149 A1* | 5/2007 | Richardson | A61M 25/0023 606/108 |
| 2007/0129603 A1 | 6/2007 | Hirsh | |
| 2007/0137651 A1 | 6/2007 | Glassenberg et al. | |
| 2007/0139953 A1 | 6/2007 | Krattiger et al. | |
| 2007/0156022 A1 | 7/2007 | Patel | |
| 2007/0162095 A1 | 7/2007 | Kimmel et al. | |
| 2007/0167686 A1 | 7/2007 | McGrath | |
| 2007/0173697 A1 | 7/2007 | Dutcher et al. | |
| 2007/0175482 A1 | 8/2007 | Kimmel et al. | |
| 2007/0179342 A1 | 8/2007 | Miller | |
| 2007/0182842 A1 | 8/2007 | Sonnenschein et al. | |
| 2007/0195539 A1 | 8/2007 | Birnkrant | |
| 2007/0197873 A1 | 8/2007 | Birnkrant | |
| 2007/0215162 A1 | 9/2007 | Glassenberg et al. | |
| 2007/0265492 A1 | 11/2007 | Sonnenschein et al. | |
| 2007/0265498 A1 | 11/2007 | Ito | |
| 2007/0276436 A1 | 11/2007 | Sonnenschein et al. | |
| 2007/0299313 A1 | 12/2007 | McGrath | |
| 2008/0004498 A1 | 1/2008 | Pecherer | |
| 2008/0009674 A1 | 1/2008 | Yaron | |
| 2008/0029100 A1 | 2/2008 | Glassenberg et al. | |
| 2008/0045801 A1 | 2/2008 | Shalman et al. | |
| 2008/0051628 A1 | 2/2008 | Pecherer | |
| 2008/0055400 A1 | 3/2008 | Schechterman et al. | |
| 2008/0064926 A1 | 3/2008 | Chen | |
| 2008/0091064 A1 | 4/2008 | Laser | |
| 2008/0097161 A1 | 4/2008 | Wang et al. | |
| 2008/0158343 A1 | 7/2008 | Schechterman et al. | |
| 2008/0158344 A1 | 7/2008 | Schechterman et al. | |
| 2008/0177146 A1 | 7/2008 | Chen | |
| 2008/0177148 A1 | 7/2008 | Chen et al. | |
| 2008/0200761 A1 | 8/2008 | Schwartz et al. | |
| 2008/0211634 A1 | 9/2008 | Hopkins et al. | |
| 2008/0236575 A1 | 10/2008 | Chuda | |
| 2008/0249355 A1 | 10/2008 | Birnkrant | |
| 2008/0249370 A1 | 10/2008 | Birnkrant et al. | |
| 2008/0294010 A1 | 11/2008 | Cooper | |
| 2008/0300475 A1 | 12/2008 | Jaeger et al. | |
| 2008/0312507 A1 | 12/2008 | Kim | |
| 2009/0022393 A1 | 1/2009 | Bar/Zohar et al. | |
| 2009/0032016 A1 | 2/2009 | Law et al. | |
| 2009/0065000 A1 | 3/2009 | Chen | |
| 2009/0114217 A1 | 5/2009 | Wulfsohn et al. | |
| 2009/0118580 A1 | 5/2009 | Sun et al. | |
| 2009/0123135 A1 | 5/2009 | Amling et al. | |
| 2009/0143645 A1 | 6/2009 | Matthes | |
| 2009/0179985 A1 | 7/2009 | Amling | |
| 2009/0187078 A1 | 7/2009 | Dunlop | |
| 2009/0192350 A1 | 7/2009 | Mejia | |
| 2009/0198111 A1 | 8/2009 | Nearman et al. | |
| 2009/0209826 A1 | 8/2009 | Sanders et al. | |
| 2009/0235935 A1 | 9/2009 | Pacey | |
| 2009/0247833 A1 | 10/2009 | Tanaka | |
| 2009/0253955 A1 | 10/2009 | Akiba | |
| 2009/0264708 A1 | 10/2009 | Pacey et al. | |
| 2009/0287059 A1 | 11/2009 | Patel | |
| 2009/0299146 A1 | 12/2009 | McGrath | |
| 2009/0318758 A1 | 12/2009 | Farr et al. | |
| 2009/0318768 A1 | 12/2009 | Tenger et al. | |
| 2009/0318769 A1 | 12/2009 | Tenger et al. | |
| 2009/0322867 A1 | 12/2009 | Carrey et al. | |
| 2010/0022829 A1 | 1/2010 | Irion et al. | |
| 2010/0022843 A1 | 1/2010 | Pecherer et al. | |
| 2010/0069722 A1 | 3/2010 | Shalman et al. | |
| 2010/0087708 A1 | 4/2010 | Chen et al. | |
| 2010/0094090 A1 | 4/2010 | Mejia | |
| 2010/0101569 A1 | 4/2010 | Kim et al. | |

(56) References Cited

U.S. PATENT DOCUMENTS

| | | |
|---|---|---|
| 2010/0121152 A1 | 5/2010 | Boedeker |
| 2010/0141744 A1 | 6/2010 | Amling et al. |
| 2010/0152541 A1 | 6/2010 | Tenger et al. |
| 2010/0168521 A1 | 7/2010 | Gandarias |
| 2010/0191054 A1 | 7/2010 | Supiez |
| 2010/0191061 A1 | 7/2010 | Simons |
| 2010/0192355 A1 | 8/2010 | Zhao et al. |
| 2010/0198009 A1 | 8/2010 | Farr et al. |
| 2010/0224187 A1 | 9/2010 | Dalton |
| 2010/0249513 A1 | 9/2010 | Tydlaska |
| 2010/0249639 A1 | 9/2010 | Bhatt |
| 2010/0256451 A1 | 10/2010 | McGrath et al. |
| 2010/0261967 A1 | 10/2010 | Pacey et al. |
| 2010/0261968 A1 | 10/2010 | Nearman et al. |
| 2010/0288272 A1 | 11/2010 | Yokota et al. |

FOREIGN PATENT DOCUMENTS

| | | |
|---|---|---|
| WO | WO 2006/102770 | 10/2006 |
| WO | WO 2008/019367 | 2/2008 |
| WO | WO 2009/130666 | 10/2009 |
| WO | WO 2010/049694 | 5/2010 |
| WO | WO 2010/066787 | 6/2010 |
| WO | WO 2010/066790 | 6/2010 |
| WO | WO 2010/100496 | 9/2010 |
| WO | WO 2010/100498 | 9/2010 |

OTHER PUBLICATIONS

Coopdech VLP-100 Video Laryngoscope advertising in fero-medic.com web page; last accessed on Aug. 31, 2010 at http://www.fero-medic.com; 1 page.

GlideScope® Ranger advertising web page; last accessed on Aug. 31, 2010 at http://www.verathon.com/gs_ranger.htm; 2 pages.

McGrath® Video Laryngoscope Series 5 advertising web page; last accessed on Aug. 31, 2010 at http://www.medtel.com.au; 2 pages.

Res-Q-Tech Res-Q-Scope® II advertising web page; last accessed Oct. 13, 2009 at http://www.res-q-tech-na.com/products.html.

Anthony J. Chipas, A Video Laryngoscope, How easy is it to use? How affordable to practice?, Outpatient Surgery Magazine, Jan. 2009, 4 pages.

E. B. Liem, et al., New options for airway management: intubating fibreoptic stylets, The Board of Management and Trustees of the British Journal of Anesthesia©, 2003, 11 pages.

Ken Yanagisawa, "How I Do It"—Head and Neck and Plastic Surgery, Color Photography of Video Images of Otolaryngological Structures Using a 35 mm SLR Camera, Laryngoscope 97, Aug. 1987, 2 pages.

J. E. Smith, et al., Teaching Fibreoptic Nasotracheal Intubation With and Without Closed Circuit Television, British Journal of Anesthesia, 1993, pp. 206-211.

Pentax Corporation, Airway Scope AWS-S100, Rigid Video Laryngoscope for Intubation, Jan. 6, 2006, 4 pages.

Coopdech, Video Laryngoscope Portable VLP-100 Specifications, webpage, Aug. 2009, 2 pages.

Truview EV02 New generation intubation devices, Truphatek.com webpage, Jan. 2007, 2 page.

Truview Premier Intubation Trainer Kit, webpage, Feb. 4, 2010, 2 pages.

Pentax Corporation, Fast Accurate Portable Airway Scope, LMA North America, Inc., May 31, 2006, 19 pages.

LMA North America, Inc., Introducing the McGrath® Video Laryngoscope, Jan. 2008, 2 pages.

LMA North America, Inc., LMA CTrach™, Product Literature, May 31, 2006, 2 pages.

Verathon Medical, GlideScope® Video Laryngoscopes Product Line, May 2006, 14 pages.

International Preliminary Report on Patentability issued in PCT/US2010/058226, issued Jun. 5, 2012, 10 pages.

* cited by examiner

VISUALIZATION INSTRUMENT

CROSS-REFERENCE TO RELATED APPLICATIONS

This application claims the benefit of priority from U.S. Patent Application Ser. No. 61/314,058 entitled INTUBATION INSTRUMENT WITH VISUALIZATION FEATURES filed on Mar. 15, 2010 and U.S. Patent Application Ser. No. 61/265,330 entitled INTUBATION SYSTEM WITH ELASTOMERIC FEATURES filed on Nov. 30, 2009, the disclosures of which are expressly incorporated by reference herein in their entirety.

FIELD OF THE DISCLOSURE

The present disclosure relates generally to a system including a visualization instrument comprising a camera to view an internal space and, more particularly, to a visualization instrument comprising a camera to examine the interior of a patient.

BACKGROUND

Visualization instruments include endoscopes, laryngoscopes, borescopes and other medical instruments designed to look inside the body of a patient. Medical visualization instruments are used in a multitude of medical procedures including laryngoscopy, rhinoscopy, bronchoscopy, cystoscopy, hysteroscopy, laparoscopy, arthroscopy, etc. Visualization instruments are also used in non-medical applications such as to investigate the internal structures of machines, buildings, and explosive devices. Laryngoscopes are used to obtain view of the vocal folds and the glottis to perform noninvasive tracheal intubations. A conventional rigid laryngoscope consists of a handle with a light source and a blade. Direct laryngoscopy is usually carried out with the patient lying on his or her back. The laryngoscope is inserted into the mouth, typically on the right side, and pushed towards the left side to move the tongue out of the line of sight and to create a pathway for insertion of an endotracheal tube. The blade may be lifted with an upwards and forward motion to move the epiglottis and make a view of the glottis possible. Once the laryngoscope is in place, the endotracheal tube may be inserted into the pathway. The blade may be provided with guide surfaces to guide the insertion of the endotracheal tube. Laryngoscopes may be outfitted with illumination devices and optical devices to provide views of the vocal cords externally of the patient's body. Optical devices include lenses, mirrors, prisms and fiberoptic fibers, all adapted to transfer an optical image. Imaging devices may also be provided to capture the optical images and display the optical images in high definition display monitors.

Stylets and other visualization instruments have also been developed. Each instrument has its own limitations such as, for example, fogging, insufficient lighting to produce a good optical image, inability to project images remotely, additional procedural steps to insert the endotracheal tube, and cost. As difficult intubations may be performed remotely from a hospital, such as at the scene of an accident or military battle, it would be desirable to provide emergency responders and others affordable equipment necessary to perform field intubations. It would be desirable to provide visualization instruments which may be discarded after a single or a limited number of uses.

SUMMARY OF THE DISCLOSURE

A visualization instrument and a method of using the visualization instrument are disclosed herein. The visualization instrument is insertable into a space to capture images representing internal views of the space. The visualization instrument comprises an insertable portion supporting an imaging sensor and a video device configured to display images corresponding to views captured by the imaging sensor.

In one exemplary embodiment of the present disclosure, a visualization instrument is provided. The visualization instrument comprising a display device; an imaging assembly including a camera and a lens, the camera including an imaging sensor, an imaging support having a distal surface and an optical cavity, the optical cavity defining a cavity opening in the distal surface, the lens and the camera sealed within the optical cavity to keep the optical cavity dry, the camera outputting a digital image stream corresponding to a plurality of views obtained through the lens; a handle portion detachably coupled to the display device; a self-contained energy source supported by one of the handle portion and the display device; and an insertable portion coupled to the handle portion and insertable into the patient, the insertable portion having a distal cavity with a distal opening at a distal end thereof, the imaging assembly received by the distal cavity and electronically coupled to the display device when the insertable portion is coupled to the handle portion and the handle portion is coupled to the display device to present images corresponding to the plurality of views with the display device.

In one example thereof, the insertable portion further comprises a guide pathway adapted for guiding a tube into a patient, the distal cavity and the guide pathway arranged laterally to each other to reduce an anterior/posterior height of the insertable portion.

In another example thereof, the handle portion and the insertable portion are integrally formed as a single piece blade.

In yet another example thereof, the insertable portion further comprises an anterior guide surface and a medial guide surface, the anterior guide surface and the medial guide surface defining a guide pathway adapted for guiding a tube into a patient. In a variation thereof, the anterior guide surface and the medial guide surface are substantially orthogonal to each other. In a further variation thereof, the tube is distinguishable in the digital image stream as the tube passes through a field of view of the lens. In another variation thereof, the guide pathway comprises a proximal portion and a distal portion, the insertable portion further comprising a posterior guide surface opposite the anterior guide surface and a lateral guide surface opposite the medial guide surface, the distal portion of the guide pathway defined by the anterior guide surface, the posterior guide surface, the medial guide surface and the lateral guide surface. In a further variation thereof, the proximal portion of the guide pathway is shorter than the distal portion.

In a further example, the insertable portion further comprises an anterior wall and a medial wall, the anterior wall and the medial wall defining a guide pathway adapted for guiding a tube into a patient, the guide pathway adjacent a side of the medial wall and the distal cavity adjacent an opposite side of the medial wall, the anterior wall having a tip portion extending distally beyond the medial wall. In a further variation thereof, the tip portion includes one or more flexural support feature. In another variation thereof, the one or more flexural support feature increases a flexural strength of the tip portion by at least 5%. In another variation thereof, the flexural support feature comprises at least one of a longitudinally aligned ridge and a transverse curvature of the tip portion.

In another example, the imaging assembly is permanently attached to the insertable portion.

In yet another example, the visualization instrument further comprises an electronic connector affixed to the insertable portion and accessible from the distal cavity, the imaging assembly operable to removably connect the connector when the imaging assembly is received by the distal cavity.

In yet another example, the visualization instrument further comprises a protrusion and a recess configured to receive the protrusion, the recess and the protrusion generating an audible sound when the handle portion couples to the display device. In a variation thereof, the visualization instrument further comprises a display device support portion supporting the display device, the handle portion includes a handle cavity adapted to receive the display device support portion thereby coupling the display device to the insertable portion, one of the protrusion and the recess are positioned on the display device support portion and the other of the protrusion and the recess are positioned inside the handle cavity.

In another exemplary embodiment of the present disclosure, a visualization instrument partially insertable into a patient is provided. The visualization instrument comprising a display device; a lens; a camera including an imaging sensor, the camera outputting a digital image stream corresponding to a plurality of views obtained through the lens; a handle portion detachably coupled to the display device; a self-contained energy source supported by one of the handle portion and the display device; and an insertable portion coupled to the handle portion and insertable into the patient, the insertable portion having a distal cavity at a distal end thereof receiving the lens and the camera, the camera electronically coupled to the display device when the insertable portion is coupled to the handle portion and the handle portion is coupled to the display device to present images corresponding to the plurality of views with the display device, the insertable portion further comprising at least two substantially non-resilient walls and at least one resilient wall, the at least two non-resilient walls and the at least one resilient wall forming a guide pathway operable to guide insertion of a tube into the patient and defining an elongate opening, the at least one resilient wall deforming when at least a portion of the tube is removed through the elongate opening.

In one example thereof, the handle portion and the insertable portion are integrally formed as a single piece blade. In one variation thereof, the blade is configured to be discarded after a single use.

In another example thereof, the guide pathway defines a proximal anterior/posterior height at one end thereof and a distal anterior/posterior height at a distal end thereof, the proximal anterior/posterior height being greater than the distal anterior/posterior height.

In a further example thereof, further comprising a distal tip extending distally beyond the lens, the distal tip includes flexural strengthening features to reduce flexure of the distal tip by at least 5% when the distal tip engages the patient's tissue. In a variation thereof, the flexural strengthening features comprise at least one of a curved profile of the distal tip along its width and a longitudinal ridge extending from a surface of the distal tip.

In yet another exemplary embodiment of the present disclosure, a visualization instrument partially insertable into a patient is provided. The visualization instrument comprising an insertable portion having guiding means for guiding insertion of a tube into a patient, the guiding means resiliently deforming when at least a portion of the tube is removed through the guiding means; attachment means for detachably coupling a display device to the insertable portion; and; imaging means for capturing a plurality of images corresponding to a field of view of the imaging means and outputting a digital image stream operable to present corresponding images with the display device.

In yet another exemplary embodiment of the present disclosure, a visualization method is provided. The visualization method comprising the steps of providing an insertable component having a camera; detachably coupling a display support component to the insertable component, the display support component sized to be held by a hand of a user and including a display device, the display support component being communicatively coupled to the camera when the display support component is coupled to the insertable component; inserting the insertable component into a target space; capturing with the camera a plurality of views corresponding to a field of view of the camera; presenting with the display device a plurality of images corresponding to the plurality of views; aligning the field of view with a target within the target space; removing the insertable component from the target space; and detaching the display support component from the insertable component. In an example thereof, the method further comprises the step of discarding the insertable component.

In yet another example thereof, the target space is an interior of a patient and the target comprises the vocal cords of the patient, and the method further comprises the step of intubating the patient using the insertable component before removing the insertable component from the target space. In a variation thereof, the insertable component comprises a resilient portion, and the removing step includes the step of resiliently deforming the resilient portion.

The features of this invention, and the manner of attaining them, will become more apparent and the invention itself will be better understood by reference to the following description of embodiments of the invention taken in conjunction with the accompanying drawings.

Corresponding reference characters indicate corresponding parts throughout the several views. Although the drawings represent embodiments of the present invention, the drawings are not necessarily to scale and certain features may be exaggerated to better illustrate and explain the embodiments. The exemplifications set out herein illustrate embodiments of the invention in several forms and such exemplification is not to be construed as limiting the scope of the invention in any manner.

DETAILED DESCRIPTION

The embodiments of the disclosure discussed below are not intended to be exhaustive or limit the invention to the precise forms disclosed in the following detailed description. Rather, the embodiments are chosen and described so that others skilled in the art may utilize their teachings.

A visualization instrument, and a method of using the instrument, are disclosed herein. In one embodiment of the visualization instrument, the visualization instrument comprises a display screen and a display screen support portion removably and electrically coupled to an insertable portion including an imaging system to acquire images of an internal space. Exemplary visualization instruments include endoscopes, laryngoscopes, and stylets. The display screen support portion and the display screen may be integrally constructed and may be reusable or disposable. In various embodiments described below, a unitary component comprising the display screen and the display screen support portion is referred to as a reusable portion denoting that in many instances it is possible, although not necessary, and perhaps desirable for economic reasons, to reuse the display screen and electronic components relating thereto. In one example thereof, the reusable portion includes a housing received in a proximal cavity of a handle coupled to the insertable portion. The display device is supported by the housing. In one variation thereof, the display device is supported by the housing at a fixed angle, preferably between 10 degrees and 30 degrees, and even more preferably between 12.5 degrees and 25 degrees, measured from a plane parallel to the posterior surface of the proximal end of the insertable portion. In another variation thereof, the display device is hinged to enable a practitioner to adjust the display angle as the visualization instrument is inserted into the patient.

In another embodiment of the visualization instrument, the insertable portion comprises a passageway or guide pathway configured to guide insertion of an elongate tubular component, e.g., an airway device, endotracheal tube and the like, and an imaging assembly disposed on or in the distal end of the insertable portion. The imaging assembly captures images of the patient which are shown with the display device. A distal end of the tubular component may also be visible in the images as the tubular component slides through the guide pathway towards the vocal cords.

Advantageously, the imaging assembly may be configured to be produced at a low cost to enable the insertable portion to function as a single-use disposable device. In one embodiment, the imaging assembly comprises a support structure or camera barrel supporting a camera integrated circuit (IC), camera, or camera-chip, an illumination device, and lenses. The imaging assembly may be inserted into a cavity located in the distal end of the insertable portion. The imaging assembly may comprise a retention device. e.g., a pin, detent, resilient elastomeric filler, screw or any other fixation device configured to securely couple the imaging assembly to the distal cavity.

A commercially available camera, such as a camera used in cellular phones and personal digital assistants (PDAs), comprises an image sensor and electronic components configured to convert pixel data captured by the image sensor to image data, e.g., digital images, and to output streams of digital images in a standard format. Image sensors may comprise CCD, CMOS sensors with active or passive pixels, or other photo sensors well known in the art. Operational signals are provided to the image sensor to control its operation. Advantageously, the cost of the disposable portion is reduced further by locating the components for providing the operational signals in the reusable portion. In one example thereof, the input/output signals are provided by signal conductors, e.g., a multi-conductor flexible ribbon. In another example thereof, a control component is provided intermediate the camera and the display driver to transform the standard image stream into a differently structured image stream conforming to the size of the display device and/or transforming the standard image stream to a different format corresponding to the format required by the display driver. In yet another example, control components supported by the reusable portion housing provide control signals to the camera to define the size of the images output by the camera.

While the embodiments of the disclosure are applicable in medical and non-medical applications, exemplary features of visualization instruments will be described below with reference to medical instruments such as laryngoscopes and stylets although the invention is not limited to medical applications and instruments.

Figure 1:
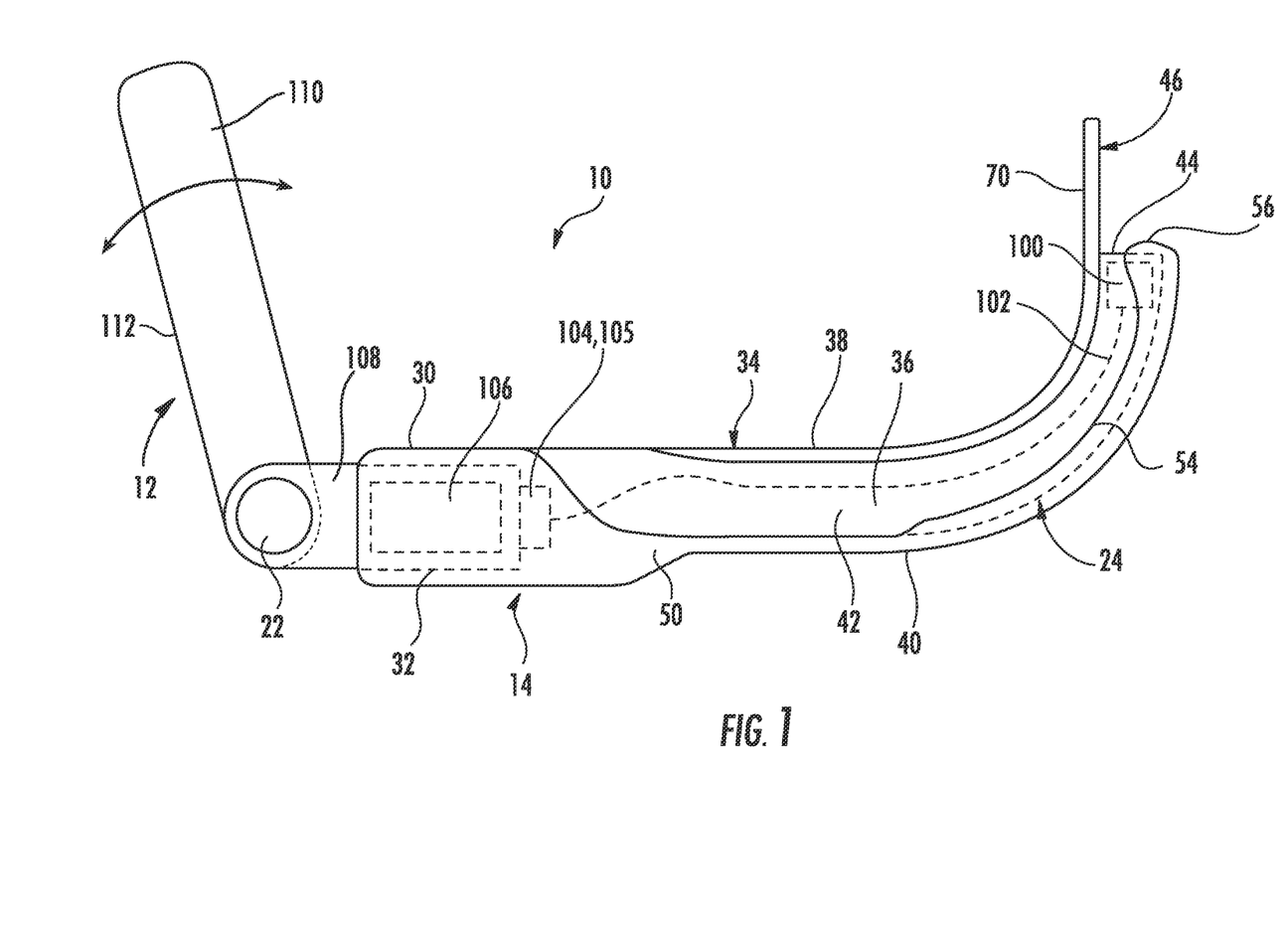
FIG. 1 is an plan view of an embodiment of a visualization instrument.

An embodiment of a visualization instrument is described below with reference to FIGS. 1 to 4. FIG. 1 is a plan view of an intubation instrument 10 comprising a reusable portion 12 having a display device 110 pivotally coupled via a hinge 22 to a housing 108 and a blade 14. Blade 14 comprises a handle 30 in a proximal end thereof spaced apart from an insertable portion located at a distal end. An imaging assembly, illustratively imaging assembly 100, is located at the distal end. In the present embodiment, the term blade denotes a single part integrally combining handle 30 and an insertable portion defined by a plurality of walls as described below. Display device 110 includes a viewing screen 112. Hinge 22 may comprise a friction hinge or may include an adjustment knob to lock display device 110 in a desired position. Handle 30 comprises a proximal cavity 32 for receiving housing 108 and coupling reusable portion 12 to blade 14. The insertable portion of blade 14 comprises an elongate passageway, illustratively passageway 36, designed to guide insertion of a catheter, intubation tube and the like (not shown) into the larynx of a patient. Housing 108 includes batteries and electronic circuits operable to receive image signals from imaging assembly 100 via a conductor 102 which comprises a plurality of signal conductors and may comprise power and control conductors as well. Housing 108 may comprise a control component 106 and a connector 104 adapted to couple with a connector 105 of blade 14 to transfer images thereto. Throughout the figures reference is made to imaging assembly 100 for exemplary purposes. Unless stated differently below, reference to imaging assembly 100 is representative and non-limiting.

Passageway 36 is defined by the interior surfaces of a medial wall 44, an anterior wall 34, a posterior wall 24, and a lateral wall 50 which in this embodiment comprises a wall portion 54. Each wall has an interior surface which is the surface adjacent to passageway 36. A surface 42 is the interior surface of medial wall 44. Surfaces 38 and 40 are the external surfaces of anterior wall 34 and posterior wall 24, respectively. In other embodiments wall 50 may extend uninterrupted from the proximal to the distal end of blade 14 or may be configured with more or fewer wall portions. Passageway 36 may have a cross-section designed to be operable with endotracheal tubes having internal diameters ranging from 2.0 to 10.0 mm, and more preferably between 5.0 and 8.0 mm. Surfaces 38 and 40 define the anterior and posterior surfaces, respectively, of blade 14. Wall 50 may also include a wall portion 56 configured to confine the volume of passageway 36 further than as confined by wall portion 54. A distal tip 46 extends wall 34 beyond the end of medial wall 44 and comprises a surface 70 which is configured to contact the patient to move the epiglottis and expose the vocal cords.

The cross-sectional area of passageway 36 may be uniform or may vary. In one embodiment, the cross-sectional area of passageway 36 is smaller at the distal end of the insertable portion than at its proximal end. One or both of walls 24 and 54, or portions thereof, may be formed at least in part of a composition comprising resilient material, e.g., thermoset or thermoplastic elastomeric material, buta-N (Nitrile) (NBR), EPDM, Silicone, Neoprene, block copolymers (SIS, SBS, SEBS, SEPS), etc., configured to enable the smaller cross-sectional area to expand when a tube is introduced through passageway 36 having a diameter which is larger than the cross-sectional area. Advantageously, a resilient distal cross-sectional area enables the insertion portion to snugly receive tubes of different diameters which are pressed against the anterior wall by the resilient material and are thereby placed by the resilient material adjacent to distal tip 46.

Still referring to FIG. 1, guide pathway 36 includes a proximal portion and a distal portion. The proximal portion extends from the proximal end of guide pathway 36 to the proximal end of wall portion 54, and the distal end is coextensive with wall portion 54. In a further variation, the proximal portion of guide pathway 36, measured along a center line of the insertion portion, is shorter than the distal portion. As seen in FIG. 1, the proximal portion length is at most 40% of the insertable portion length.

In one example, the medial guide surface includes a transition portion extending through the proximal portion of the guide pathway and a longitudinally aligned portion extending through the distal portion of the guide pathway. In a variation thereof, the transition portion extends from a lateral side of the insertable portion to the longitudinally aligned portion.

In another embodiment of a visualization instrument, the visualization instrument comprises audible engagement features. In one example thereof, a protrusion makes an audible sound when it engages a notch to indicate to a user that the handle and the display device have been properly engaged. In another example, ridges or channels comprise an interruption adapted to receive a protrusion and to make an audible sound when the protrusion is received by the interruption. In a further example, a protrusion supported by a support element supporting a display device, and a matching recess in the handle are configured to generate an audible sound, such as a "click" sound, when the handle and the support element are properly engaged.

Figure 2:
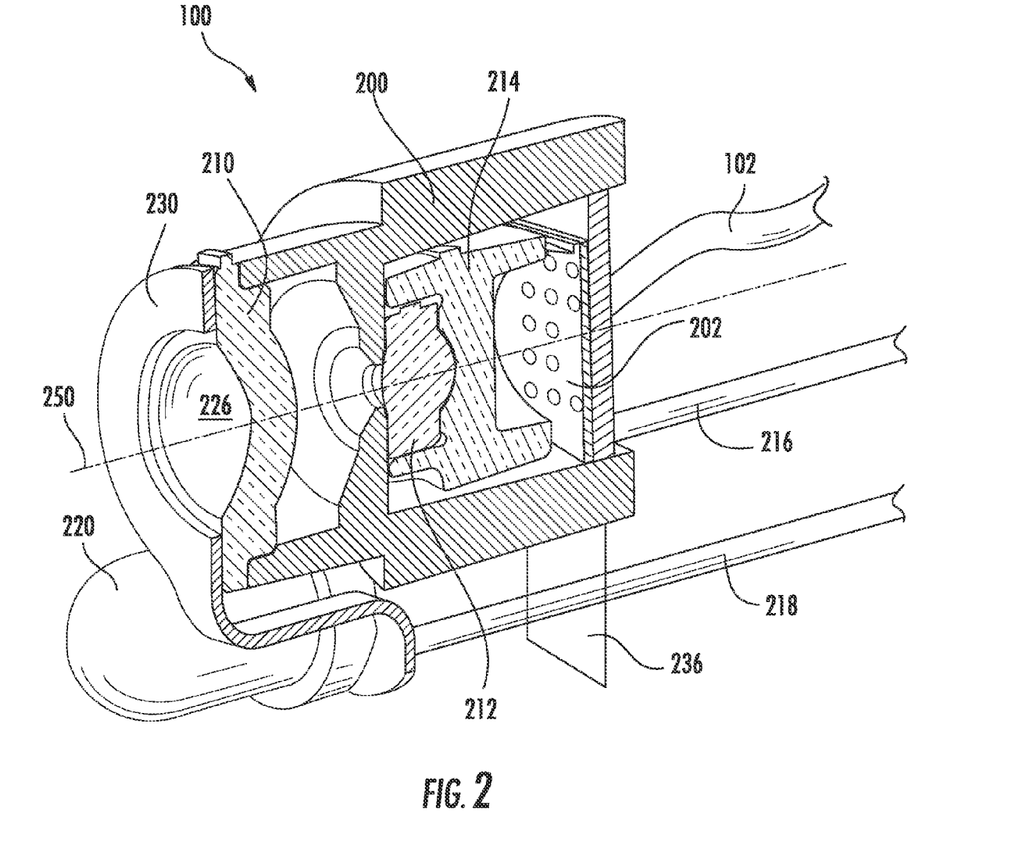
FIG. 2 is a cross-sectional perspective view of an embodiment of an imaging assembly.

FIG. 2 is a cross-sectional perspective view of imaging assembly 100. Imaging assembly 100 comprises a plurality of lenses supported by a camera barrel 200. A heating element 230 supports an illumination device 220 which, as shown, comprises an LED powered by connectors 216 and 218. The LED may be over-driven to provide power in excess of that which is necessary to produce the maximum illumination output of the device. The excess power generates heat which is transferred to heating element 230 and a distal lens 210 to reduce fogging. Camera barrel 200 also supports a lens 212 and a lens 214. Images corresponding to spaces viewable by distal lens 210 are sensed by a camera 202 which comprises a sensing array and circuitry to output an image stream comprising pixel data. A support prong 236 is provided proximally adjacent to camera 202 to secure under pressure imaging assembly 100 to blade 14.

Figure 3:
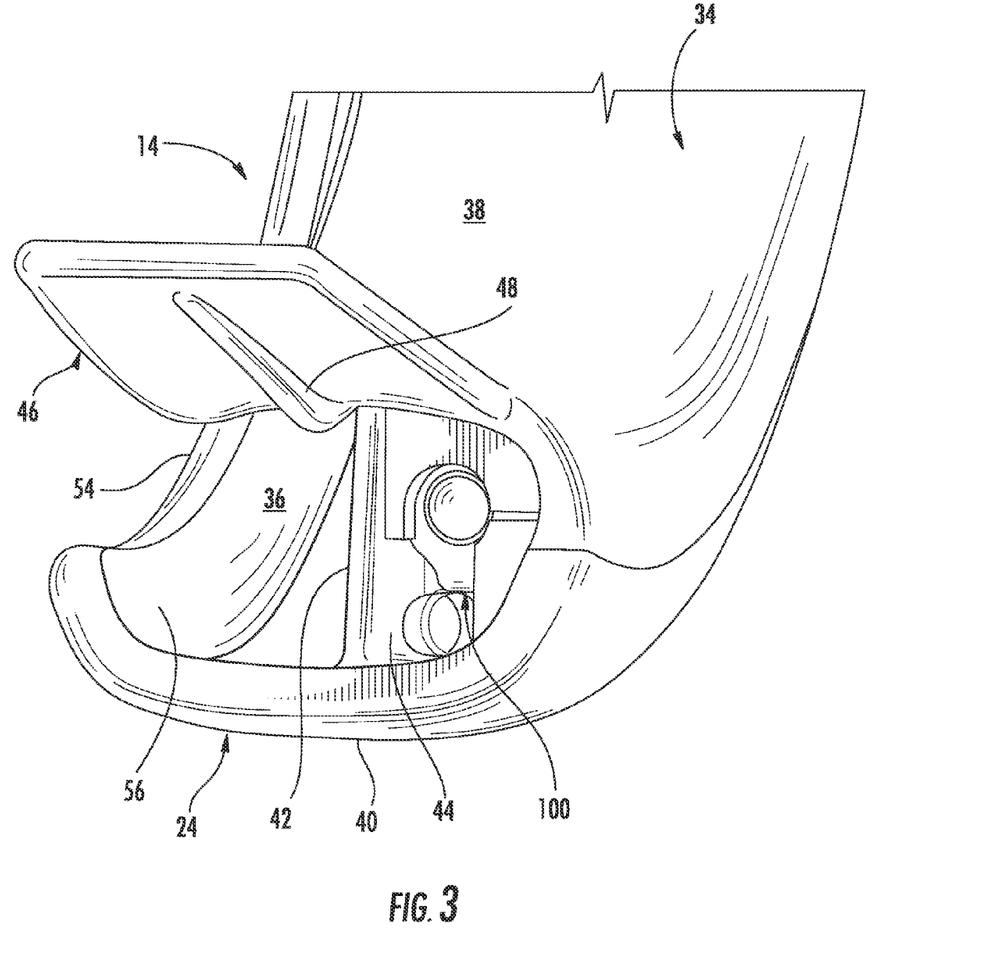
FIG. 3 is a partial perspective view of the visualization instrument of FIG. 1 illustrating the imaging assembly of FIG. 2.
Figure 4:
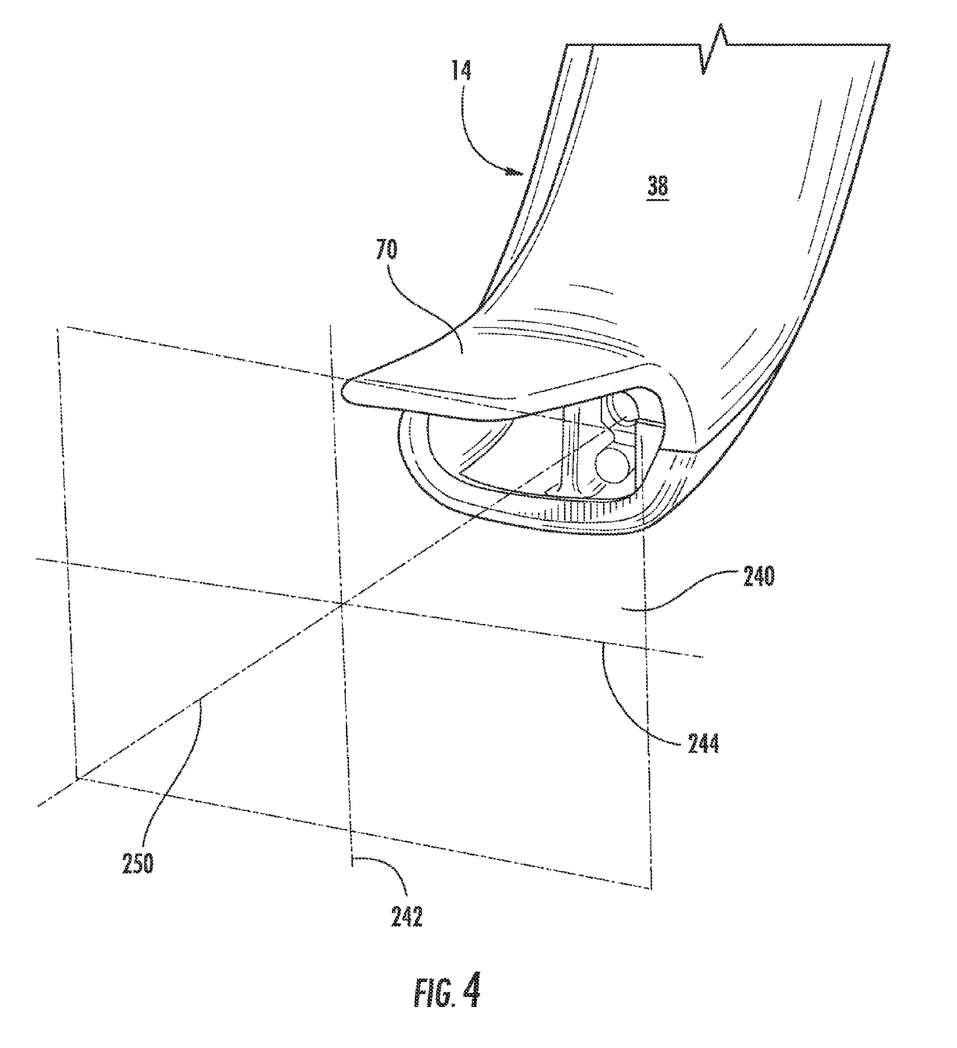
FIG. 4 is a partial perspective view of the visualization instrument of FIG. 1 illustrating the imaging assembly of FIG. 2 and a view obtainable with the imaging assembly.

FIG. 3 is a partial perspective view of blade 14. As shown, the distal end of blade 14 comprises passageway 36 on one side of medial wall 44 and imaging assembly 100 inserted in a distal cavity on the opposite side. A longitudinally aligned ridge 48 is shown (also shown in FIG. 6) extending from a surface of distal tip 46. FIG. 4 illustrates a viewing area 240 oriented perpendicular to distal surface 226 of distal lens 210 with a center line 250 passing through the center of viewing area 240 at the crossing of a medial/lateral (M/L) center line 242 and an anterior/posterior (A/P) center line 244 indicating the direction of view (DOV) of camera 202. It is desirable to view the insertion of the endotracheal tube through the vocal cords. Thus, imaging assembly 100 may be angled with respect to medial wall 44 to obtain an angled DOV. In another example, distal lens 210 and/or lenses 212 and 214 are angled with respect to medial wall 44 and/or each other to provide an angled DOV while retaining imaging assembly 100 parallel to medial wall 44. Advantageously, lenses may be angled to enable placing imaging assembly 100 in a smaller cavity thereby reducing the size and cost of blade 14 even further. In a further example, center line 250 and imaging assembly 100 are oriented parallel to surface 70 and between 10 degrees and 25 degrees towards passageway 36 relative to medial wall 44. In the embodiment shown, blade 14 comprises an anterior and a posterior part which may be injection molded and thereafter joined together.

Figure 5:
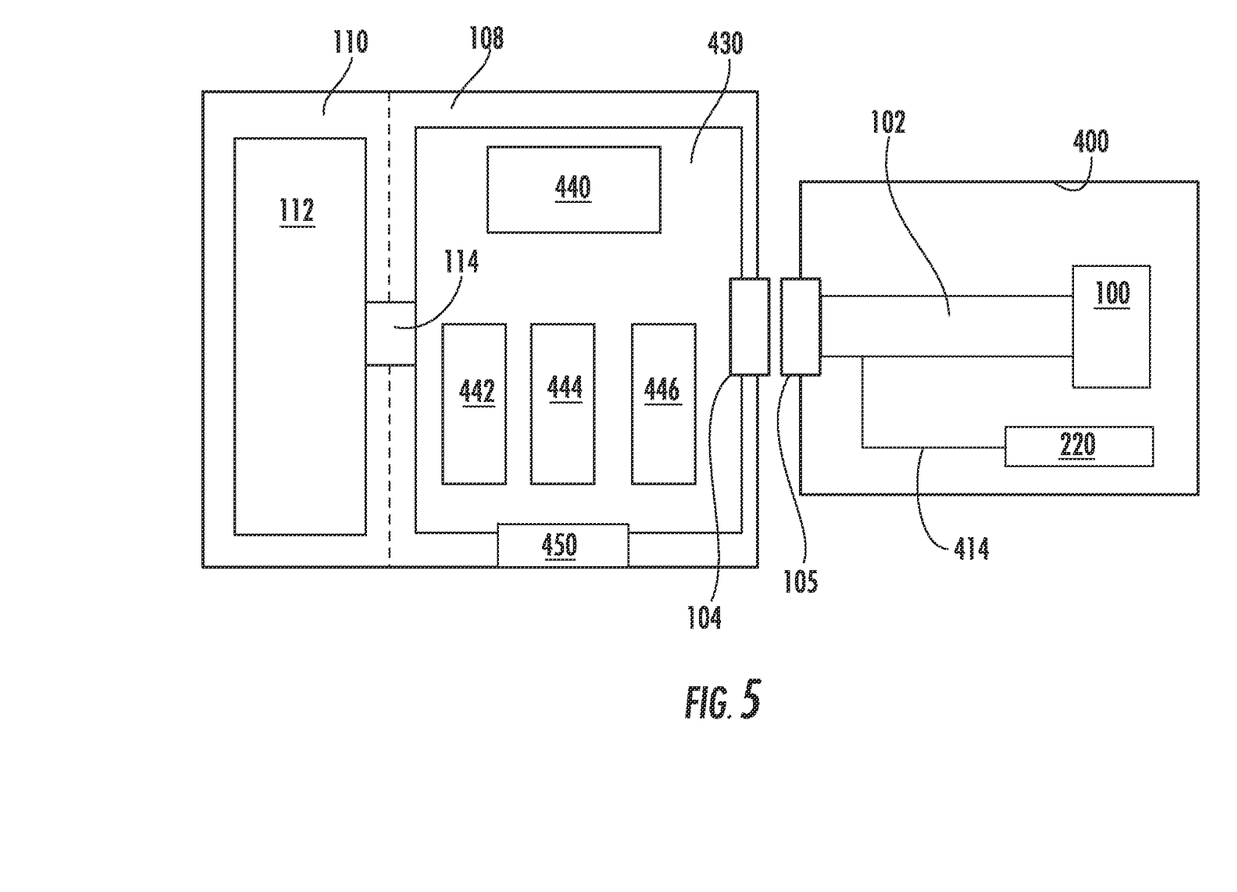
FIG. 5 is a block diagram of an embodiment of electronic components of a visualization instrument.

FIG. 5 is a block diagram of electronic components of an embodiment of a visualization device. The device comprises an imaging assembly, illustratively imaging assembly 100, disposed in an insertable portion, illustratively a support 400, and electronically coupled to housing 108 by conductor 102 and connectors 104 and 105. Support 400 also includes illumination device 220 which is energized via illumination power connectors 414. A control component 430 comprises one or more circuit boards containing electronic components such as a chip 440, illustratively a field programmable gate array (FPGA), a chip 442, illustratively a NTSC/S-video conversion IC, and optionally a video processing chip and memory, illustratively a video chip 444 and a memory chip 446, respectively. Control component 430 controls the operation of camera 202 by providing operational signals. It also receives a first image stream from camera 202 and converts it to a format suitable for display unit 110, which is coupled to control component 430 by conductors or connectors 114. Optionally, control component 430 may convert the first image stream to a format suitable for an external display and for remote transmission, for example through a communications port 450. For example, control component 430 may sample images to reduce the amount of information transmitted to a remote device. Of course, if the first image stream is suitable to display device 110, then conversion is not necessary. Control component 430 may provide operational signals for display device 110. Such signal may also be generated by components incorporated in display device 110.

In one example of the present embodiment, the camera supplies a first image stream which is 8-bits wide. The resolution of the camera is 640×480 (VGA) pixels per frame. There are 30 frames per second. The data format is 2 bytes per pixel (i.e., the so called YUV (4:2:2) format). Intensity Y is specified at every pixel, color information U or V every second time. A FPGA is programmed to convert the data stream to a second image stream with a format compatible with the display device 110 which comprises an OLED display. In an alternative embodiment, the camera data is provided to the video processing chip, and the video processing chip, after adding information such as colors, symbols or other information, outputs a video stream to the FPGA for the FPGA to convert to the VGA format. The display resolution is 320×240 (QVGA) pixels per frame, 30 frames per second. The data format, however, is RGB (6, 6, 6). This format uses a 6-bit value for red, a 6-bit value for green, and a 6-bit value for blue. There are specific well known equations for conversion from the YUV color space to the RGB color space. The FPGA implements this conversion. It also performs the conversion (e.g. dropping every second pixel) to convert from VGA to QVGA resolution. The FPGA also provides signals for writing the converted data stream into the OLED display's memory/buffer. The FPGA also sends the camera data to the NTSC/S-video conversion chip. The video chip having the video processor is capable of accepting the VGA, YUV format almost directly. The FPGA provides the necessary operational signals to load the video chip's memory.

A program and data structures are embedded in the memory. The program comprises a plurality of processing sequences operable by the processor to interact with data structures containing data. Data may include parameters such as video instructions and the like.

In yet another embodiment of the visualization instrument, comfort features are provided. In one example thereof, the handle comprises soft material to enhance grasping comfort. In another example, the insertion portion comprises a resilient component to reduce pressure on the teeth of the patient. In a further example thereof, a blade comprises a first material which imparts structure and rigidity to the insertable portion and a second material coupled to the first material to provide a soft and resilient feel. In one variation, the second material extends, at least partially, over the surface of the handle. For example, a thin layer of elastomeric material, e.g., about 1 mm thick, may be provided over surface 40 and extend to the posterior side of handle 30. The second material may also extend over the surface of wall 50. The second material may be adhesively secured to the first material. The first material has a first modulus and the second material has a second modulus which is lower than the first modulus. In a further example, walls 34 and 44 comprise the first material and wall portion 54 comprises the second material. Advantageously, this embodiment provides flexibility to wall portion 54 which facilitates removal of the endotracheal tube from passageway 36.

Figure 6:
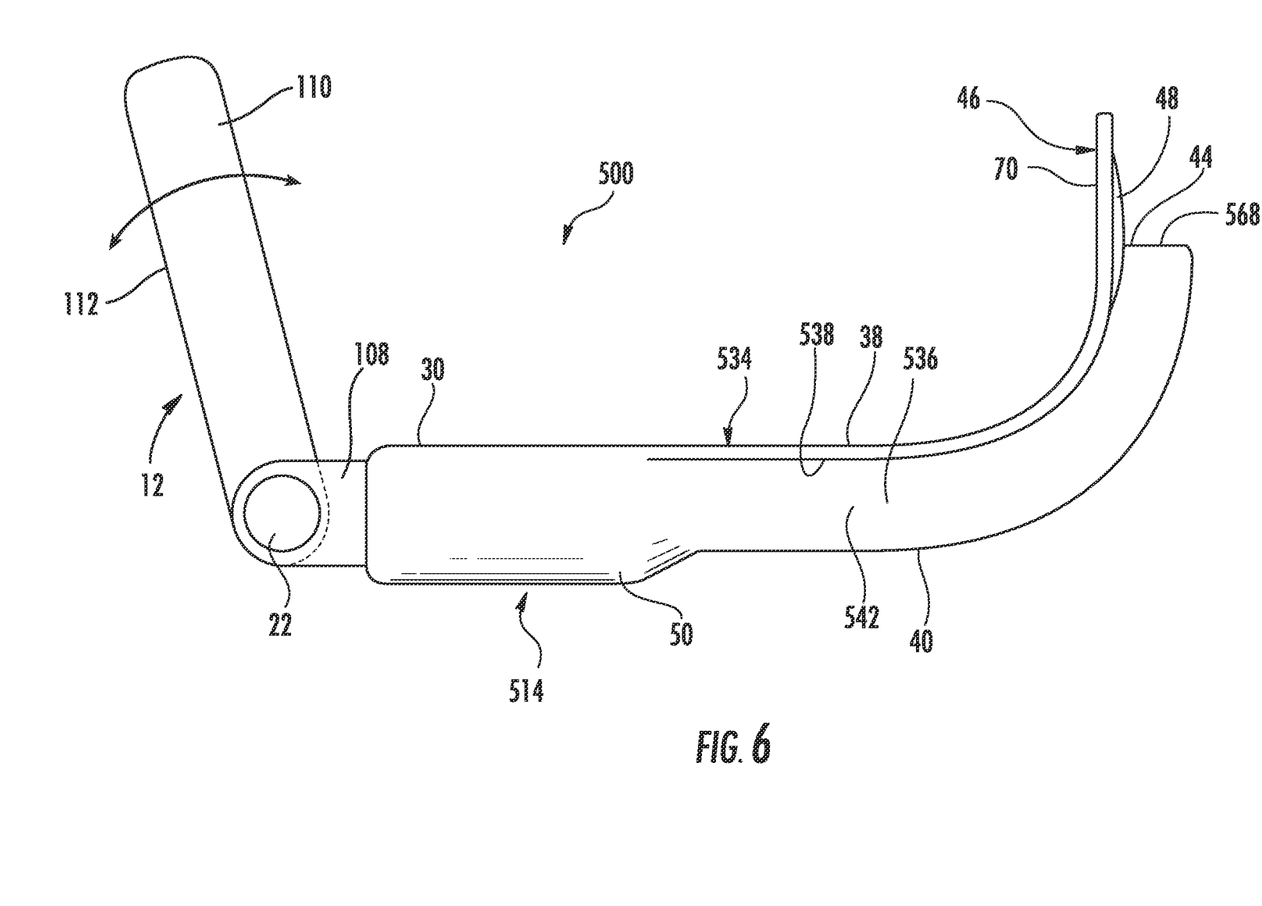
FIG. 6 is a plan view of another embodiment of a visualization instrument.

Another embodiment of a visualization instrument, denoted by numeral 500, is described below with reference to FIG. 6. Intubation instrument 500 comprises reusable portion 12 having display device 110 pivotably coupled via hinge 22 to housing 108 and blade 514 having handle 30 in a proximal end spaced apart from a distal end having distal cavity 568 in which imaging assembly 100 is located. Blade 514 comprises passageway 536 which is designed to guide insertion of a catheter into the larynx of a patient. Passageway 536 is defined by interior surface 542 of medial wall 44 and interior surface 538 of anterior wall 534.

Figure 7:
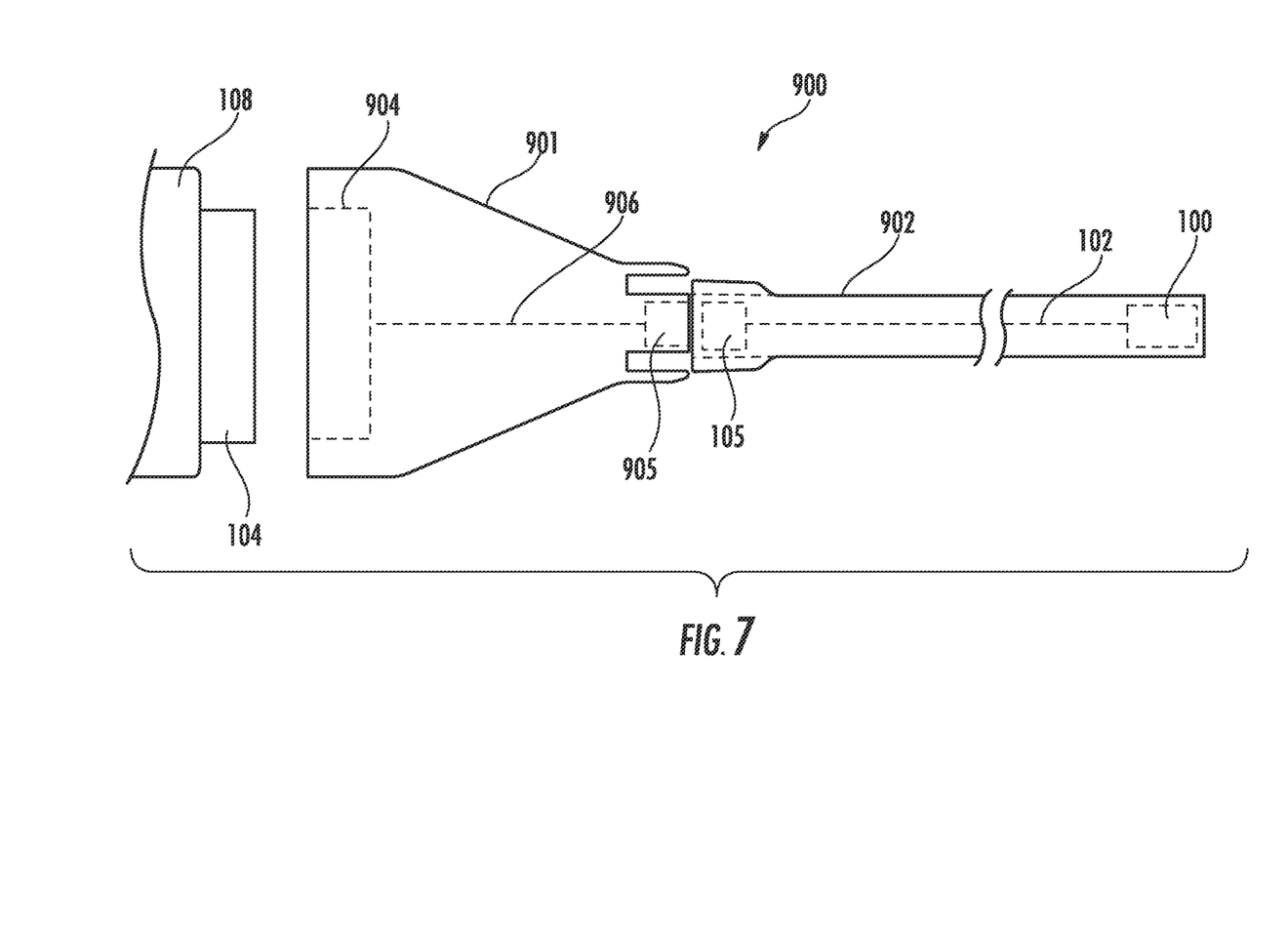
FIG. 7 is an elevation view of a further embodiment of a visualization instrument.

FIG. 7 is a plan view of another visualization instrument, denoted by numeral 900. Intubation instrument 900 is configured to receive an endotracheal tube over an insertable portion, illustratively stylet 902, which is removably coupled to an adapter 901 configured to connect stylet 902 and housing 108. Adapter 901 comprises a conductor 906 electrically coupling connectors 904 and 905. The diameter of stylet 902 may range between 2 mm and 7 mm, preferably between 3 mm and 6 mm. Stylet 902 may comprise a malleable material adapted to retain a longitudinal shape and facilitate introduction of imaging assembly 100 into the cavity of interest.

While the invention has been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this invention pertains.

The invention claimed is:

1. A visualization instrument comprising:
a display device;
a housing coupled to the display device, the housing configured to contain a battery;
a lens;
a camera including an imaging sensor, the camera outputting an image stream corresponding to a plurality of views obtained through the lens, the display device operable to display the plurality of views; and
a blade including a handle portion and an insertable portion, the insertable portion having a distal cavity housing the camera and the handle portion including a handle cavity adapted to detachably couple with the housing to support the display device, wherein the battery is positioned in the handle cavity when the housing is coupled to the blade,
wherein the insertable portion comprises an anterior wall having an anterior guide surface and a medial wall having a medial guide surface, the anterior guide surface and the medial guide surface forming a guide pathway adapted for guiding a tube into a patient, the guide pathway located on one side of the medial wall and the distal cavity located on the opposite side of the medial wall, the anterior wall having a tip portion extending distally beyond the medial wall and including a flexural support feature, and
wherein the flexural support feature includes a longitudinally aligned ridge protruding from the anterior guide surface along the tip portion of the anterior wall between longitudinal borders of the tip portion of the anterior wall.

2. The visualization instrument of claim 1, wherein the flexural support feature further comprises a transverse curvature of the tip portion.

3. The visualization instrument of claim 1, wherein the imaging sensor is permanently attached to the insertable portion.

4. The visualization instrument of claim 1, further comprising a protrusion and a recess configured to receive the protrusion, the recess and the protrusion generating an audible sound when the recess receives the protrusion indicating proper coupling of the blade and the display device.

5. The visualization instrument of claim 4, the protrusion and the recess generating the audible sound when the handle cavity receives the housing.

6. The visualization instrument of claim 1, the insertable portion further comprising a posterior wall having a posterior guide surface opposite the anterior guide surface, the guide pathway including a proximal portion and a distal portion, only the distal portion including a lateral wall extending anteriorly from the posterior wall, the lateral wall and the anterior wall forming an elongate opening through which the tube can be removed.

7. The visualization instrument of claim 6, wherein the proximal portion of the guide pathway is shorter than the distal portion of the guide pathway.

8. The visualization instrument of claim 7, wherein the length of the proximal portion is at most 40% of the length of the insertable portion, measured along a center line of the insertable portion.

9. The visualization instrument of claim 7, further including a transition surface extending along the proximal portion of the guide pathway from a lateral side of the insertable portion to the medial guide surface.

10. The visualization instrument of claim 6,
wherein the insertable portion includes a resilient portion including the lateral wall,
wherein the resilient portion is operable to deform when at least a portion of the tube is removed through the elongate opening, and
wherein the anterior wall of the blade is more rigid than the lateral wall.

11. The visualization instrument of claim 10, wherein the resilient portion enables the insertable portion to snugly receive tubes of different diameters which are pressed against the anterior wall by the resilient portion.

12. The visualization instrument of claim 11, wherein the anterior wall of the blade is more rigid than the resilient portion to facilitate displacement of a tissue of a patient.

13. The visualization instrument of claim 12, wherein the resilient portion is formed from a resilient material and the anterior wall of the blade is formed from a more rigid material than the resilient material.

14. The visualization instrument of claim 13, wherein the resilient portion is affixed to a rigid structure of the insertable portion formed by the anterior wall and the medial wall.

15. The visualization instrument of claim 1, wherein the flexural support feature further includes concave surfaces on a surface opposing the anterior guide surface and along the longitudinal borders of the tip portion of the anterior wall.

16. A visualization instrument comprising:
a display device;
a lens;
a camera including an imaging sensor, the camera outputting an image stream corresponding to a plurality of views obtained through the lens, the display device operable to display the plurality of views;
a blade detachably coupled to the display device, the blade including a handle portion and an insertable portion, the insertable portion having a distal cavity housing the camera,
wherein the insertable portion comprises a guide pathway formed by
an anterior wall having an anterior guide surface;
a medial wall having a medial guide surface; and
at least one resilient wall,
the guide pathway operable to guide insertion of a tube into a patient and comprising an elongate opening,
the at least one resilient wall operable to deform when at least a portion of the tube is removed through the elongate opening,
wherein the anterior wall of the blade is more rigid than the at least one resilient wall.

17. The visualization instrument of claim 16, the insertable portion further comprising a posterior wall having a posterior guide surface opposite the anterior guide surface, the guide pathway including a proximal portion and a distal portion, only the distal portion including a lateral wall extending anteriorly from the posterior wall, the lateral wall and the anterior wall forming the elongate opening.

18. The visualization instrument of claim 17, wherein the at least one resilient wall comprises the lateral wall.

19. The visualization instrument of claim 17, wherein the proximal portion of the guide pathway is shorter than the distal portion of the guide pathway.

20. The visualization instrument of claim 17, wherein the length of the proximal portion is at most 40% of the length of the insertable portion, measured along a center line of the insertable portion.

21. The visualization instrument of claim 17, further including a transition surface extending along the proximal portion of the guide pathway from a lateral side of the insertable portion to the medial guide surface.

22. The visualization instrument of claim 16, further comprising a housing adapted to contain a battery, the housing permanently coupled to the display device, wherein the handle includes a proximal cavity configured to receive the housing to detachably couple the blade and the display device, and wherein the battery is positioned in the proximal cavity when the housing is coupled to the blade.

23. The visualization instrument of claim 16, wherein the at least one resilient wall enables the insertable portion to snugly receive tubes of different diameters which are pressed against the anterior wall by the at least one resilient wall.

24. The visualization instrument of claim 23, wherein the anterior wall of the blade is more rigid than the at least one resilient wall to facilitate displacement of a tissue of a patient.

25. The visualization instrument of claim 24, wherein the at least one resilient wall is formed from a resilient material and the anterior wall of the blade is formed from a more rigid material than the resilient material.

26. The visualization instrument of claim 25, wherein the at least one resilient wall is affixed to a rigid structure of the insertable portion including the anterior wall and the medial wall.

27. The visualization instrument of claim 16,
wherein the at least one resilient wall is formed from a resilient material and the anterior wall of the blade is formed from a more rigid material than the resilient material, and
wherein the at least one resilient wall is affixed to a rigid structure of the insertable portion formed by the anterior wall and the medial wall.

28. A visualization instrument comprising:
a display device;
a lens;
a camera including an imaging sensor, the camera outputting an image stream corresponding to a plurality of views obtained through the lens, the display device operable to display the plurality of views;
a blade detachably coupled to the display device, the blade including a handle portion and an insertable portion, the insertable portion having a distal cavity housing the camera,
wherein the insertable portion comprises a guide pathway operable to guide insertion of a tube into a patient, the guide pathway comprising a proximal portion and a distal portion,
the proximal portion and the distal portion including an anterior wall having an anterior guide surface;
the proximal portion and the distal portion including a medial wall having a medial guide surface;

only the distal portion including a posterior wall having a posterior guide surface opposite the anterior guide surface and a lateral wall extending anteriorly from the posterior wall, the lateral wall and the anterior wall forming an elongate opening through which the tube can be removed, wherein the insertable portion includes a resilient portion including the lateral wall, the resilient portion being operable to deform when at least a portion of the tube is removed through the elongate opening, and wherein the anterior wall of the blade is more rigid than the lateral wall.

29. The visualization instrument of claim 28, wherein the proximal portion of the guide pathway is shorter than the distal portion of the guide pathway.

30. The visualization instrument of claim 29, wherein the length of the proximal portion is at most 40% of the length of the insertable portion, measured along a center line of the insertable portion.

31. The visualization instrument of claim 28, further including a transition surface extending along the proximal portion of the guide pathway from a lateral side of the insertable portion to the medial guide surface.

32. The visualization instrument of claim 28, further comprising a housing adapted to contain a battery, the housing permanently coupled to the display device, wherein the handle includes a proximal cavity configured to receive the housing to detachably couple the blade and the display device, and wherein the battery is positioned in the proximal cavity when the housing is coupled to the blade.

33. The visualization instrument of claim 28, wherein the resilient portion enables the insertable portion to snugly receive tubes of different diameters which are pressed against the anterior wall by the resilient portion.

34. The visualization instrument of claim 33, wherein the anterior wall of the blade is more rigid than the resilient portion to facilitate displacement of a tissue of a patient.

35. The visualization instrument of claim 34, wherein the resilient portion is formed from a resilient material and the anterior wall of the blade is formed from a more rigid material than the resilient material.

36. The visualization instrument of claim 35, wherein the resilient portion is affixed to a rigid structure of the insertable portion including the anterior wall and the medial wall.

37. The visualization instrument of claim 28,
wherein the resilient portion is formed from a resilient material and the anterior wall of the blade is formed from a more rigid material than the resilient portion, and
wherein the resilient portion is affixed to a rigid structure of the insertable portion including the anterior wall and the medial wall.

38. The visualization instrument of claim 28, wherein, within the proximal portion of the blade, the medial guide surface forms an open longitudinal edge that extends between the handle portion of the blade and the distal portion of the insertable portion of the blade, such that the posterior wall is separated from the handle portion by the medial wall within the proximal portion of the blade.

39. The visualization instrument of claim 10,
wherein the resilient portion is formed from a resilient material and the anterior wall of the blade is formed from a more rigid material than the resilient material, and
wherein the resilient portion is affixed to a rigid structure of the insertable portion formed by the anterior wall and the medial wall.

* * * * *